(12) United States Patent
Barbieru et al.

(10) Patent No.: US 7,776,106 B2
(45) Date of Patent: Aug. 17, 2010

(54) DYESTUFFS AND HAIR DYE COMPOSITIONS

(75) Inventors: Roxana Barbieru, Frankfurt (DE); Werner Russ, Floersheim-Wicker (DE); Dominic Pratt, Buettelborn (DE); Hartmut Moehring, Seeheim-Jugenheim (DE)

(73) Assignees: Dystar Textilfarben GmbH & Co., Deutschland KG, Frankfurt (DE); Kao Corporation, Tokyo (JP)

( * ) Notice: Subject to any disclaimer, the term of this patent is extended or adjusted under 35 U.S.C. 154(b) by 0 days.

(21) Appl. No.: 12/279,003

(22) PCT Filed: Feb. 2, 2007

(86) PCT No.: PCT/EP2007/051041

§ 371 (c)(1),
(2), (4) Date: Dec. 3, 2008

(87) PCT Pub. No.: WO2007/090799

PCT Pub. Date: Aug. 16, 2007

(65) Prior Publication Data

US 2009/0217466 A1  Sep. 3, 2009

(30) Foreign Application Priority Data

Feb. 9, 2006  (EP) .................... 06101466

(51) Int. Cl.
*A61Q 5/10* (2006.01)
*C09B 1/16* (2006.01)
(52) U.S. Cl. .............. 8/405; 8/406; 8/426; 552/237
(58) Field of Classification Search ............ 8/405, 8/406, 426; 552/237
See application file for complete search history.

(56) References Cited

U.S. PATENT DOCUMENTS

| 3,442,895 A | 5/1969 | Bugaut et al. |
| 3,531,502 A | 9/1970 | Kalopissis et al. |
| 5,486,629 A * | 1/1996 | Chan et al. .......... 552/236 |

FOREIGN PATENT DOCUMENTS

| EP | 0 818 193 | 1/1998 |
| EP | 0 852 136 | 7/1998 |
| GB | 1 005 913 | 9/1965 |
| GB | 1123095 | 8/1968 |
| GB | 1 205 365 | 9/1970 |

OTHER PUBLICATIONS

STIC Search Report dated Dec. 8, 2009.*
U.S. Appl. No. 12/278,715, filed Aug. 7, 2008, Barbieru, et al.
* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

The present invention refers to dyestuffs of the general Formula (I) wherein R, X, Y and Z are defined as given in claim 1, dyestuff mixtures and hair dye compositions comprising them, as well as a process for coloring hair.

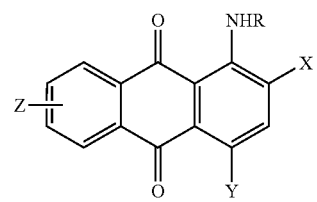

(I)

6 Claims, No Drawings

DYESTUFFS AND HAIR DYE COMPOSITIONS

The present invention relates to anthraquinone hair dyes and hair dye compositions containing them.

Hair dyes can be classified by the dye to be used therefore, or by whether they have bleaching action of melanin or not. Typical examples include a two-part permanent hair dye composed of a first part containing an alkali agent, an oxidation dye and optionally a direct dye such as a nitro dye and a second part containing an oxidizing agent; and a one-part semi-permanent hair dye containing an organic acid or an alkali agent, and an acid dye, basic dye or direct dye such as a nitro dye.

The above-described permanent hair dye is however accompanied by the drawback that the color tone imparted by an oxidation dye is not so vivid and that they damage the hair. Use of a nitro dye or cationic dye for a two-component hair dye containing an oxidizing agent has been attempted in order to produce various color tones (refer to, for example, Japanese Patent Laid-Open No. 1994-271435 and EP 1 133 976 A2). A permanent hair dye formulation containing current direct dyes typically develop a vivid color just after dyeing, but the color fades away quickly over time and which leads to a dull end result. Also the use of many direct dyes involves such problems as decomposition when mixed with a peroxide serving as an oxidizing agent and incompatibility with the formulation.

The above described semi-permanent hair dye formulations are accompanied by the drawback that the color imparted typically displays low durability. In addition, it is difficult to achieve violet, blue and ash tones since the number of dyes which can deliver these tones is extremely limited. Such dyes must be high performing and toxicologically safe.

It is known to use quaternized anthraquinone dyes to dye hairs, see for example DE 1 203 915, DE 1 248 865, DE 1 492 066, GB 1 205 365, U.S. Pat. No. 3,531,502, EP 0 818 193 A2 and EP 0 852 136 A1. In addition, U.S. Pat. No. 3,657,213, GB 1,270,107, GB 1,248,652, U.S. Pat. Nos. 2,888,467, 2,737,517, 4,246,172, CH 14851/71, DE 16 19 365, CH 463666, FR 1,363,216, U.S. Pat. No. 5,486,629 and GB 807 241 teach to dye textile materials with quaternized anthraquinone dyes.

However, there is still a need for hair dyes which can effectively deliver blue, ash, violet or red tones to the hair without damaging and are toxicologically safe.

It was now surprisingly found that specific anthraquinone dyes according to the definition given below provide the required properties.

Accordingly, the present invention provides dyestuffs of the general formula (I)

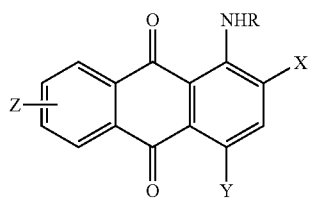

(I)

wherein

R is hydrogen, alkyl, alkyl substituted by Q, aryl, Q-aryl, —$OR^2$, —$SR^3$ or —$NR^5R^4$, hydroxyalkyl, hydroxyalkyl substituted in the alkyl group by Q, polyhydroxyalkyl, polyhydroxyalkyl substituted in the alkyl group by Q, cycloalkyl, cycloalkyl substituted by Q, aryl substituted by $R^{10}$, Q, $R^{11}$O-alkyl, —$OR^{12}$, —$SR^{13}$—$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$, —$C(O)R^6$, —$SO_2NR^7R^8$ or —$SO_2R^9$;

X is hydrogen, —$OR^{23}$, —$SR^{24}$—$NR^{25}R^{26}$, —$SO_2NR^{27}R^{28}$, —$CONR^{29}R^{30}$, —$S_2OR^{31}$, —$C(O)OR^{32}$, —$C(O)R^{33}$—$SO_2R^{34}$, alkyl, alkyl substituted by —$OR^{200}$, —$SR^{300}$ or —$NR^{500}R^{400}$, aryl substituted by $R^{100}$, $R^{110}$O-alkyl, —$OR^{120}$—$SR^{130}$, —$NR^{140}R^{150}$, —$CONR^{150}R^{160}$, —$C(O)OR^{170}$, —$SO_2$—$NR^{180}R^{190}$, —$SO_2OR^{201}$—$C(O)R^{210}$ or —$S^{220}$, —$NHSO_2R^{36}R^{37}$, —CHO, —CH=$NR^{35}$ or $NO_2$;

Y is hydrogen, —$NR^{51}R^{52}$, —$OR^{53}$, —$SR^{54}$, —$SO_2NHR^{55}$, —$NHC(O)R^{56}$, —$SO_2OR^{57}$, —$NHSO_2R^{58}$, —$SO_2R^{59}$, —$NHSO_2NR^{60}R^{61}$, halogen or $NO_2$;

Z is hydrogen, —$NR^{51}R^{52}$, —$OR^{53}$, —$SR^{54}$, —$SO_2NHR^{55}$, —$NHC(O)R^{56}$, —$SO_2OR^{57}$, —$NHSO_2R^{58}$, —$SO_2R^{59}$, —$NHSO_2NR^{60}R^{61}$, halogen or $NO_2$;

each of $R^2$ to $R^8$, $R^{60}$ and $R^{61}$, independently, is hydrogen, alkyl, alkyl substituted by Q, aryl, aryl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

$R^9$ is alkyl, alkyl substituted by Q, aryl, aryl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{10}$ to $R^{16}$, $R^{18}$, $R^{19}$ and $R^{21}$ independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{17}$, $R^{20}$ and $R^{22}$ independently, is alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{23}$ to $R^{30}$ and $R^{35}$, independently, is hydrogen, alkyl, hydroxyalkyl, polyhydroxyalkyl, cycloalkyl or cycloalkyl substituted by —$C(O)R^{6'}$, —$SO_2R^{9'}$, or aryl substituted by $R^{10'}$, $R^{11'}$O-alkyl, —$OR^{12'}$, —$SR^{13'}$, —$NR^{14'}R^{15'}$, —$CONR^{15'}R^{16'}$, —$C(O)OR^{17'}$, —$SO_2$—$NR^{18'}R^{19'}$, —$SO_2OR^{20'}$, —$C(O)R^{21'}$ or —$SO_2R^{22'}$;

$R^{6'}$ is hydrogen, alkyl, aryl, hydroxyalkyl, polyhydroxyalkyl or cycloalkyl;

$R^{9'}$ is alkyl, aryl, hydroxyalkyl, polyhydroxyalkyl or cycloalkyl;

each of $R^{10'}$ to $R^{16'}$, $R^{18'}$, $R^{19'}$ and $R^{21'}$, independently, is hydrogen, alkyl, hydroxyalkyl, polyhydroxyalkyl or cycloalkyl;

each of $R^{17'}$, $R^{20'}$ and $R^{22'}$, independently, is alkyl, hydroxyalkyl, polyhydroxyalkyl or cycloalkyl;

each of $R^{36}$ and $R^{37}$, independently, is alkyl, aryl, hydroxyalkyl, polyhydroxyalkyl or cycloalkyl and one of $R^{36}$ and $R^{37}$ can additionally be hydrogen;

each of $R^{51}$ to $R^{54}$, independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q, —$C(O)R^6$, —$SO_2R^9$, or aryl substituted by $R^{10}$, $R^{11}$O-alkyl, —$OR^{12}$, —$SR^{13}$, —$NR^{14}R^{15}$, —$CONR^{15}R^{16}$—$C(O)OR^{17}$, —$SO_2$—$NR^{18}R^{19}$, —$SO_2OR^{20}$, —$C(O)R^{21}$ or —$SO_2R^{22}$;

each of $R^{31}$ to $R^{33}$, independently, is alkyl, hydroxyalkyl, polyhydroxyalkyl, cycloalkyl or aryl substituted by $R^{10'}$, $R^{11'}$O-alkyl, —$OR^{12'}$, —$SR^{13'}$, —$NR^{14'}R^{15'}$, —$CONR^{15'}R^{16'}$, —$C(O)OR^{17'}$, —$SO_2$—$NR^{18'}R^{19'}$, —$SO_2OR^{20'}$, —$C(O)R^{21'}$ or —$SO_2R^{22'}$, and $R^{33}$ can additionally be hydrogen;

$R^{34}$ is alkyl, hydroxyalkyl, polyhydroxyalkyl, cycloalkyl or aryl substituted by $R^{10'}$, $R^{11'}$O-alkyl, —$OR^{12'}$, —$SR^{13'}$, —$NR^{14'}R^{15'}$, —$CONR^{15'}R^{16'}$, —$C(O)OR^{17'}$, —$SO_2$—$NR^{18'}R^{19'}$, —$SO_2OR^{20'}$, —$C(O)R^{21'}$ or —$SO_2R^{22'}$;

each of $R^{55}$ to $R^{57}$, independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q or aryl substituted by $R^{10}$, $R^{11}$O-alkyl, —$OR^{12}$, —$SR^{13}$, —$NR^{14}R^{15}$, —$CONR^{15}R^{16}$, —$C(O)OR^{17}$, —$S_2$—$NR^{18}R^{19}$, —$SO_2OR^{20}$, —$C(O)R^{21}$ or —$SO_2R^{22}$ and $R^{55}$ and $R^{56}$ can additionally be hydrogen;

each of $R^{58}$ and $R^{59}$, independently, is alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q or aryl substituted by $R^{10}$, $R^{11}$O-alkyl, —$OR^{12}$, —$SR^{13}$, —$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$;

each of $R^{200}$, $R^{300}$, $R^{400}$ and $R^{500}$, independently, is hydrogen, alkyl, aryl, hydroxyalkyl, polyhydroxyalkyl or cycloalkyl;

each of $R^{100}$, $R^{110}$, $R^{120}$, $R^{130}$, $R^{140}$, $R^{150}$, $R^{160}$, $R^{180}$, $R^{190}$ and $R^{210}$, independently, is hydrogen, alkyl, hydroxyalkyl, polyhydroxyalkyl, or cycloalkyl;

each of $R^{170}$, $R^{201}$ and $R^{220}$, independently, is alkyl, hydroxyalkyl, polyhydroxyalkyl, or cycloalkyl; and Q is a group of the general formula (II)

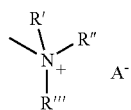

(II)

wherein each of R', R" and R'", independently, is $(C_1$-$C_6)$-alkyl, aryl, arylalkyl, cycloalkyl, cycloalkylalkyl, heteroaryl, heteroarylalkyl, heterocycloalkyl, heterocycloalkyl-alkyl, either of which can be substituted by heteroatom containing groups or R' and R" form together with the nitrogen to which they are bonded a 5- or 6-membered saturated heterocyclic ring; and $A^-$ is a cosmetically acceptable, water solubilizing anion, and does not comprise arylsulfonate, phosphonate and alkylphosphonate;

whereby the dyestuff of the formula (I) contains exactly one group Q;

whereby at least two of the groups X, Y and Z are groups other than hydrogen; and whereby in case R and X are both hydrogen and Y is —$NR^{51}R^{52}$ or —$OR^{23}$, wherein $R^{51}$, $R^{52}$ and $R^{23}$ are hydrogen, Z is not —$NR^{25}R^{26}$, wherein one of $R^{25}$ and $R^{26}$ is hydrogen and the other is alkyl substituted by Q.

Alkyl groups may be straight-chain or branched and are preferably $(C_1$-$C_6)$-alkyl, for example methyl, ethyl, n-propyl, isopropyl, n-butyl, n-pentyl, isopentyl or n-hexyl.

Cycloalkyl is preferably $(C_3$-$C_8)$-cycloalkyl and especially preferably cyclopentyl and cyclohexyl.

Aryl groups are preferably phenyl or naphthyl groups.

Halogen is preferably chlorine, bromine and fluorine.

A 5- or 6-membered saturated heterocyclic ring which is formed by R' and R" is preferably a pyrrolidine, piperidine, morpholine or piperazine ring. R', R" and R'" are preferably benzyl or $(C_1$-$C_6)$-alkyl and especially preferably benzyl, methyl and ethyl.

The dyestuffs of the general formula (I) may be salts of an organic or inorganic acid. Consequently, $A^-$ may be for example chloride, bromide, iodide, hydroxide, hydrogenphosphate, phosphate, carbonate, hydrogencarbonate, hydrogensulfate, perchlorate, fluoroborate, chlorozincate, methylsulfate, ethylsulfate, acetate, propionate, lactate or citrate or mixtures thereof.

The meaning of $A^-$ is generally given by the preparation method of the dyestuff of the general formula (I). Preferred meanings of $A^-$ are chloride, sulfate, hydrogensulfate, methylsulfate, ethylsulfate, phosphate, formate, acetate and lactate.

Especially preferred dyestuffs of the present invention are dyestuffs of the general formula (I) in which X is $(C_1$-$C_6)$-alkyl, —$OR^{23}$ or —$SR^{24}$, wherein $R^{23}$ and $R^{24}$ are hydrogen, $(C_1$-$C_6)$-alkyl, hydroxy-$(C_1$-$C_6)$-alkyl or phenyl, or —$CONR^{29}R^{30}$ or —$C(O)OR^{32}$, wherein $R^{29}$ and $R^{30}$, independently are hydrogen, $(C_1$-$C_6)$-alkyl, hydroxy-$(C_1$-$C_6)$-alkyl or phenyl and $R^{32}$ is $(C_1$-$C_6)$-alkyl, hydroxy-$(C_1$-$C_6)$-alkyl or phenyl;

Z is hydrogen;

R is hydrogen or $(C_1$-$C_6)$-alkyl;

Y is —$NR^{51}R^{52}$ or —$OR^{53}$, wherein $R^{51}$ is hydrogen and $R^{52}$ is $(C_1$-$C_6)$-alkyl substituted by Q, phenyl substituted by Q or $(C_1$-$C_6)$-alkyl-$SO_2$-phenyl wherein the alkyl group is substituted by Q; and $R^{53}$ is $(C_1$-$C_6)$-alkyl substituted by Q, phenyl substituted by Q, $(C_1$-$C_6)$-alkyl-$SO_2$-phenyl wherein the alkyl group is substituted by Q or $(C_1$-$C_6)$-alkyl-NH—$SO_2$-phenyl wherein the alkyl group is substituted by Q;

Q is a tris-$(C_1$-$C_6)$-alkyl-ammonium group, a bis$(C_1$-$C_6)$-alkyl-benzyl-ammonium group, a methyl-morpholinium group or a methyl-pyrrolidinium group; and $A^-$ is chloride, sulfate, hydrogensulfate, methylsulfate, ethylsulfate, phosphate, formate, acetate or lactate.

Examples of dyestuffs of this type are the dyestuffs of the formulae (Ia), (Ib), (Id)-(Ih), (Ir), (Is) and (Ix).

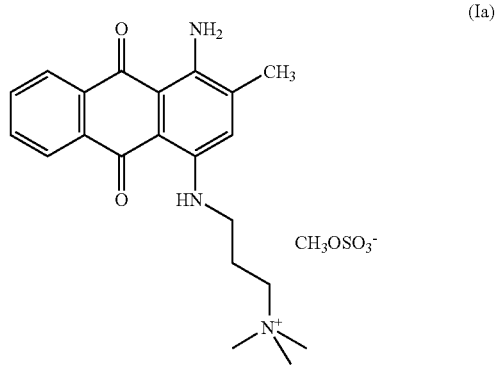

(Ia)

-continued
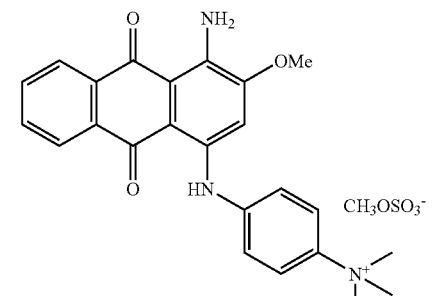
(Ib)
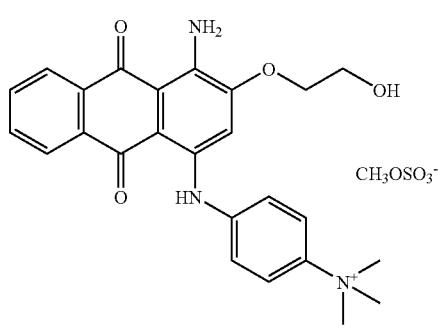
(Id)
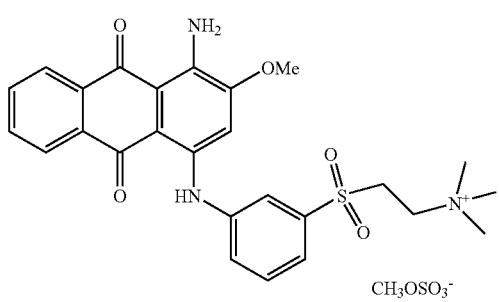
(Ie)
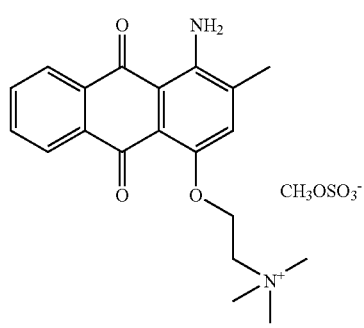
(If)
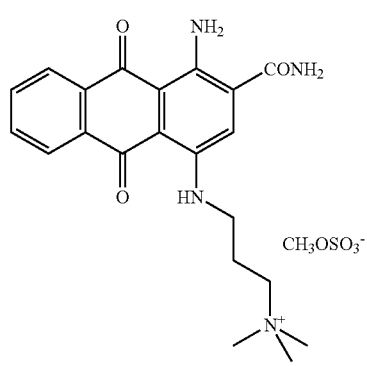
(Ig)
-continued
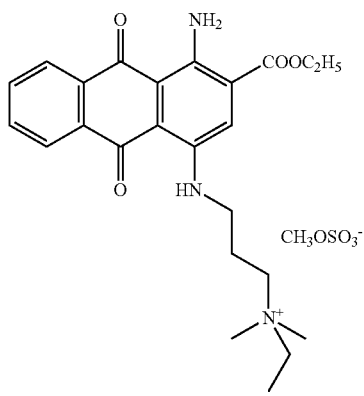
(Ih)
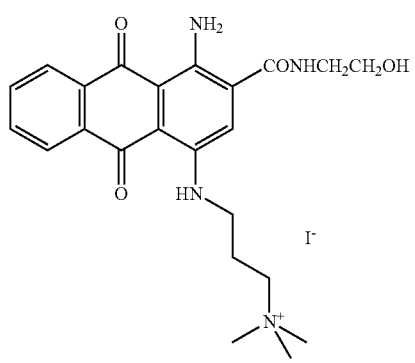
(Ir)
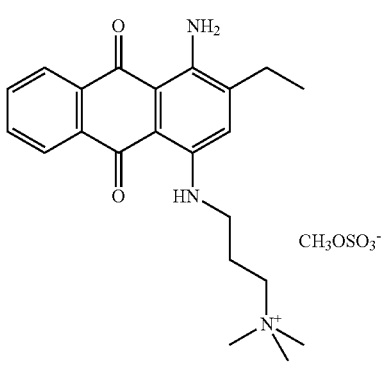
(Is)
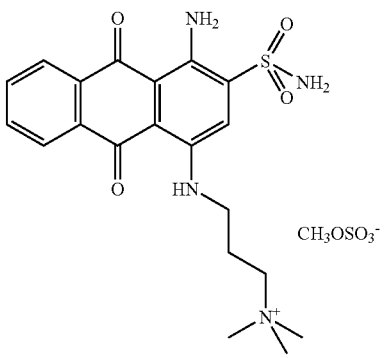
(Ix)
Further especially preferred dyestuffs of the present invention are dyestuffs of the general formula (I) in which
Z is —$NR^{51}R^{52}$, —$NHC(O)R^{56}$ or —$OR^{53}$, wherein $R^{51}$ is hydrogen $R^{52}$ and $R^{53}$ are hydrogen or ($C_1$-$C_6$)-alkyl substituted by Q and $R^{56}$ is ($C_1$-$C_6$)-alkyl or phenyl;

X is hydrogen;

R is hydrogen or $(C_1-C_6)$-alkyl;

Y is $-NR^{51}R^{52}$ or $-OR^{53}$, wherein $R^{51}$ is hydrogen, $R^{52}$ is hydrogen, $(C_1-C_6)$-alkyl, hydroxy-$(C_1-C_6)$-alkyl, $(C_1-C_6)$-alkyl substituted by Q, phenyl, phenyl substituted by Q or $(C_1-C_6)$-alkyl-$SO_2$-phenyl wherein the alkyl group is substituted by Q; and $R^{53}$ is hydrogen, $(C_1-C_6)$-alkyl, $(C_1-C_6)$-alkyl substituted by Q, phenyl, phenyl substituted by Q, $(C_1-C_4)$-alkyl-$SO_2$-phenyl wherein the alkyl group is substituted by Q or $(C_1-C_4)$-alkyl-NH—$SO_2$-phenyl wherein the alkyl group is substituted by Q;

Q is a tris-$(C_1-C_6)$-alkyl-ammonium group, a bis$(C_1-C_6)$-alkyl-benzyl-ammonium group, a methyl-morpholinium group or a methyl-pyrrolidinium group which is bonded to either Z or Y; and $A^-$ is chloride, sulfate, hydrogensulfate, methylsulfate, ethylsulfate, phosphate, formate, acetate or lactate.

Examples of dyestuffs of this type are the dyestuffs of the formulae (Ij) to (In) and (It) to (Iu) and (Iy)

(Ij)
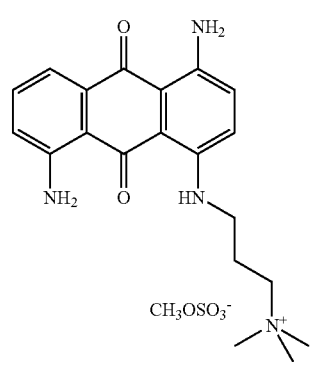

(Ik)
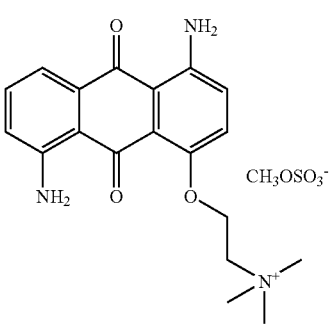

(Il)
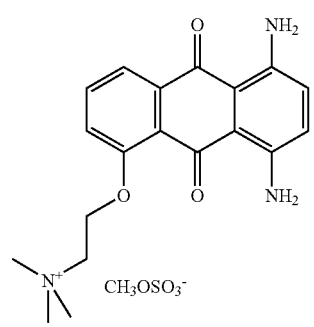

(Im)
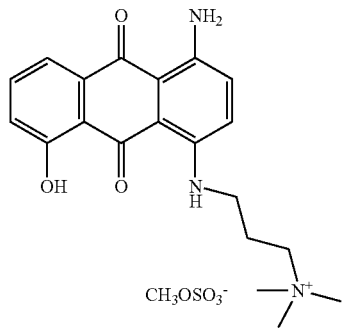

(In)
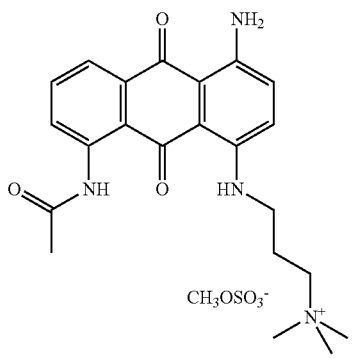

(It)
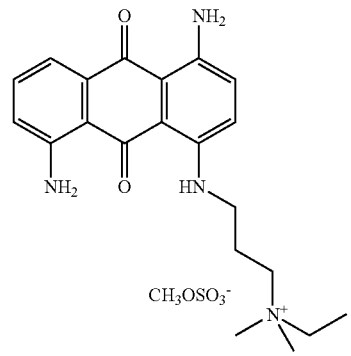

(Iu)
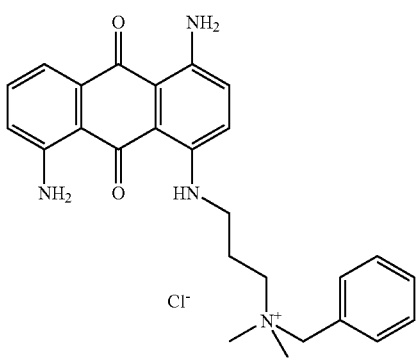

-continued (Iy)

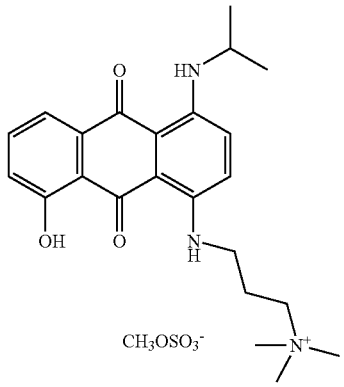

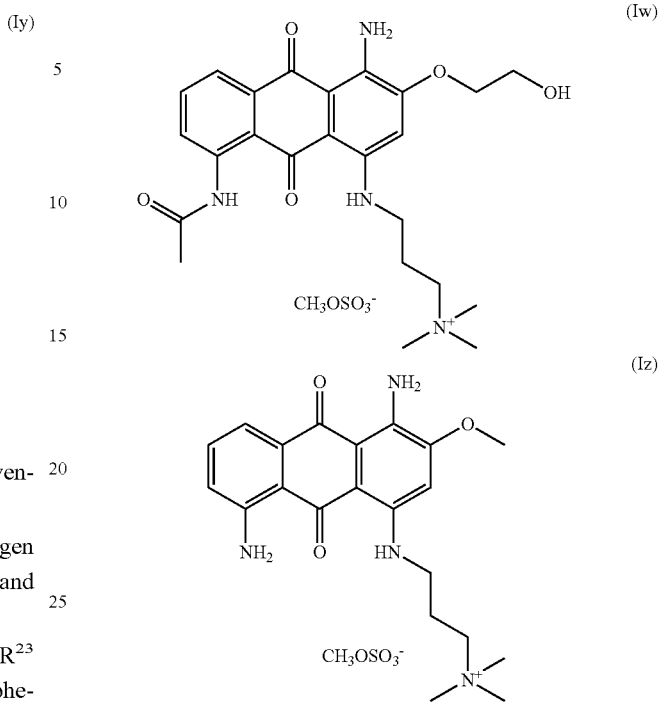

Further especially preferred dyestuffs of the present invention are dyestuffs of the general formula (I) in which Z is —NR$^{51}$R$^{52}$, —NHC(O)R$^{56}$, wherein R$^{51}$ is hydrogen and R$^{52}$ is hydrogen or (C$_1$-C$_6$)-alkyl substituted by Q and R$^{56}$ is (C$_1$-C$_6$)-alkyl or phenyl;

X is —OR$^{23}$, —SO$_2$NR$^{27}$R$^{28}$ or —SO$_2$OR$^{31}$, wherein R$^{23}$ and R$^{31}$ are (C$_1$-C$_6$)-alkyl, hydroxy(C$_1$-C$_6$)-alkyl or phenyl; R$^{27}$ is hydrogen, R$^{28}$ is hydrogen (C$_1$-C$_6$)-alkyl or hydroxy(C$_1$-C$_6$)-alkyl;

R is hydrogen or (C$_1$-C$_6$)-alkyl;

Y is —NR$^{51}$R$^{52}$, wherein R$^{51}$ is hydrogen, R$^{52}$ is (C$_1$-C$_6$)-alkyl, (C$_1$-C$_6$)-alkyl substituted by Q, hydroxy-(C$_1$-C$_6$)-alkyl, hydroxy-(C$_1$-C$_6$)-alkyl substituted in the alkyl group by Q, phenyl or phenyl substituted by Q;

Q is a tris(C$_1$-C$_6$)-alkyl-ammonium group, a bis(C$_1$-C$_6$)-alkyl-benzyl-ammonium group, a methyl-morpholinium group or a methyl-pyrrolidinium group which is bonded to either Y or Z; and A$^-$ is chloride, sulfate, hydrogensulfate, methylsulfate, ethylsulfate, phosphate, formate, acetate or lactate.

Examples of dyestuffs of this type are the dyestuffs of the formulae (Iv), (Iw) and (Iz):

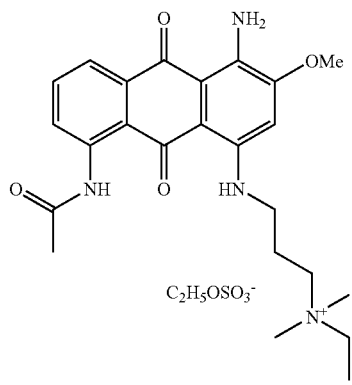

(Iv)

The dyestuffs of the general formula (I) can be obtained by generally known methods, for instance via Ullmann type substitutions of anthraquinone derivatives which contain exchangeable atoms or groups such as halogen, sulfonic acid group or nitro group by aliphatic amines, aromatic amines, alcohols, phenols, thiols, thiophenols and sulfur containing reagents. General procedures are described, for example, in "Ullmann's Encyclopedia of Industrial Chemistry", VCH Verlagsgesellschaft, Weinheim 1985, volume A2, Anthraquinone Dyes and Intermediates, pages 357-412. The preparing reactions of the dyestuffs can be carried out in an organic solvent such as dimethylformamide, dimethylacetamide, halogenobenzenes etc., in water or preferably in surplus reagent. It is of advantage to carry out the reactions at elevated temperatures, preferably between 60° C. and 150° C. Acid-binding agents must be added or an excess of amine is used. Adding usual catalysts such as copper or copper salts or mixtures thereof can be advantageously.

The alkoxyanthraquinones of the general formula (I) can be obtained via the conversion of anthraquinonesulfonic acids by alcoholic alkali at 50-130° C. The direct replacement of halogen to alkoxy- or aryloxyanthraquinones can be advantageously carried out with e.g. alcoholate or phenolate generated in situ with alkali or advantageously with metallic sodium. It is advantageously to carry out these reactions under water free conditions with dried reagents.

The present invention also refers to dyestuff mixtures comprising one or more dyestuffs of the general formula (I) according to the present invention and one or more direct or oxidation dyestuff.

Examples of such direct dyes include dyes from the publicly available dyestuff list issued by The European Cosmetic, Toiletry and Perfumery Association (COLIPA) and especially Acid Yellow 1, Disperse Red 17, Basic Brown 17, Acid Black I, 4-Nitro-o-phenylenediamine, Picramic acid, HC Red 13, N,N-bis(2-hydroxyethyl)-2-nitro-p-phenylenediamine, HC Red 7, HC Blue 2, HC Yellow 4, HC Yellow 2, HC Orange 1, HC Red 1, HC Red 3,4-Amino-3-nitrophenol, 2-Hydroxyethylamino-5-nitroanisole, 3-Nitro-p-hydroxyethylaminophenol, 3-Methylamino-4-nitrophenoxytheanol, 2-nitro-5-glyceryl methylaniline, HC Violet 1, HC Orange 2, HC Yellow 9, 4-Nitrophenylaminoethylurea, HC Red 10, HC Red 11, 2-Hydroxy-ethyl picramic acid, HC Blue 12, Hydroxyethyl-2-nitro-p-toluidine, HC Blue 11, HC Yellow 7, HC Yellow 10, 4-Amino-2-nitrophenylamine-2-carboxylic acid, 2-Chloro-6-ethylamino-4-nitrophenol, HC Violet 2,2-Amino-6-chloro-4-nitrophenol, 4-Hydroxypropylamino-3-nitrophenol, HC Yellow 13, 2,6-Diamino-3-((pyridin-3-yl)azo) pyridine, N-(2-nitro-4-aminophenyl)-allylamine, Basic Violet 2, Basic Red 51, Basic Yellow 87, Basic Orange 31, Basic Red 76, Basic Brown 16, Basic Yellow 57, Acid Orange 7, Acid Red 33, Acid Yellow 23, Acid Blue 9, Acid Red 92, Acid Yellow 3, Acid Violet 43, Disperse Violet 1, Acid Blue 62, Disperse Black 9, Hydroxyanthraquinoneaminopropylmethyl morpholinium methosulfate, Lawsone, HC Blue 14, Curry Red, Acid Red 18, Acid Red 52, Acid Green 25, Disperse Blue 377, Pigment Red 57, HC Blue 15, Tetrabromophenol Blue, Basic Blue 7, Basic Blue 26, Basic Blue 99, Basic Violet 10, Basic Violet 14; cationic dyes as described in Japanese Patent Laid-Open Nos. 2204/1983, 118832/1997 and Japanese Laid-Open Publications (PCT) Nos. 501322/1996 and 507545/1996 (please check numbers); and methine type cationic dyes having a cyanine structure.

The inventive dyestuff mixtures of the present invention usually contain one or more dyestuffs of the general formula (I) in an amount 90 to 10 wt. % and one or more direct or oxidation dyestuff in an amount of 10 to 90 wt. % based on the total weight of the dyestuff mixture.

Preferably, the inventive dyestuff mixtures contain one or more dyestuffs of the general formula (I) in an amount 80 to 20 wt. % and one or more direct or oxidation dyestuff in an amount of 20 to 80 wt. % based on the total weight of the dyestuff mixture.

Especially preferably, the inventive dyestuff mixtures contain one or more dyestuffs of the general formula (I) in an amount 65 to 35 wt. % and one or more direct or oxidation dyestuff in an amount of 35 to 65 wt. % based on the total weight of the dyestuff mixture.

The dyestuffs of the general formula (I) as defined above, as well as dyestuff mixtures comprising one or more dyestuffs of the general formulae (I) and one or more direct or oxidation dyestuff can advantageously be used to dye hair, especially human hair.

The present invention also refers to hair dye compositions comprising one or more dyestuffs of the general formulae (I). Such hair dye compositions usually contain the dyestuffs of the general formulae (I) in amounts of 0.0001 to 20 wt. %, preferably 0.001 to 20 wt. %, more preferably from 0.01 to 10 wt. % and especially preferably from 0.05 to 5 wt. %, based on the weight of the hair dye composition.

Furthermore, the present invention also refers to hair dye compositions comprising one or more dyestuffs of the general formulae (I) and one or more direct or oxidation dyestuff.

Hair dye compositions containing a dyestuff mixture as described above usually have a dyestuff content between 0.001 to 20 wt. %, preferably from 0.01 to 20 wt. %, more preferably from 0.05 to 10 wt. % and especially preferably from 0.1 to 5 wt. %, based on the weight of the hair dye composition.

In the hair dye compositions according to the present invention, the inventive dyestuffs of the general formula (I) exhibit a high storage stability within a wide pH range from 2 to 11, which is a pH range ordinarily employed for hair dyes, so that the hair dye composition of the present invention can be used at any pH in the above-described pH range. Use in a pH range of from 2 or greater is however preferred from the viewpoint of dyeing property. Hair dye compositions of a pH range of 2 to 8 and hair dye compositions of a pH range of 8 to 12 are preferred.

The desired pH value is usually adjusted using an alkali agent. Examples of alkali agents include ammonia, alkanolamines such as monoethanolamine and isopropanolamine or salts thereof, guanidium salts such as guanidine carbonate and hydroxides such as sodium hydroxide. The inventive hair dye compositions contain an alkali agent preferably in an amount of from 0.01 to 20 wt. %, more preferably from 0.1 to 10 wt. %, especially preferably from 0.5 to 5 wt. % based on the total weight of the composition.

Since the inventive dyestuffs of the formula (I) have high stability against oxidizing agents, the inventive hair dye composition may also be applied to hair together with an oxidizing agent. In other words, it can be provided as a two-part composition composed of a first part containing the dyestuff of the general formula (I) and a second part containing an oxidizing agent. In this case, hair dyeing and bleaching can be carried out simultaneously, which facilitates more vivid hair dyeing. Examples of oxidizing agent include hydrogen peroxide, persulfates such as ammonium persulfate, potassium persulfate and sodium persulfate, perborates such as sodium perborate, percarbonates such as sodium percarbonate and bromates such as sodium bromate and potassium bromate. Hydrogen peroxide is especially preferred from the viewpoints of hair bleaching property, stability and effectiveness of the inventive dyestuffs of the general formula (I). Hydrogen peroxide may be used in combination with another oxidizing agent. The oxidizing agent is preferably used in an amount of from 0.5 to 10 wt. %, especially preferably from 1 to 8 wt. %, based on the hair dye composition.

The first part containing the inventive dyestuff of the general formula (I) and the second part containing the oxidizing agent are mixed at a volume ratio preferably ranging from 2:1 to 1:3.

In the hair dye composition of the present invention, an oxidation dye can be used in combination with the inventive dyestuff of the general formula (I). Such combined use enables considerably vivid and intense dyeing which cannot be accomplished by the single use of the oxidation dye. For the oxidation dye, known developers and couplers ordinarily employed for an oxidation type hair dye can be used. Examples of the developer include paraphenylenediamine, toluene-2,5-diamine, 2-chloro-paraphenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-para-phenylenediamine, 4,4'-diaminodiphenylamine, 1,3-bis(N-(2-hydroxyethyl)-N-(4-aminophenyl)amino)-2-propanol, PEG-3,2,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine and 4,5-diamino-1-(4'-chlorobenzyl)pyrazole and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene, 1,3-bis(2,4-diaminophenoxy)propane, metaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine, and 2,6-diaminopyridine and salts thereof.

As each of the developer and coupler, at least two of the above-described developers or couplers are usable. The content of each of them is preferably from 0.01 to 20 wt. %, especially preferably from 0.05 to 10 wt. % based on the hair dye composition.

To the hair dye composition of the present invention, an autoxidation dye typified by an indole or an indoline, or a known direct dye such as a nitro dye or a disperse dye can also be added.

Addition of a polyol, polyol alkyl ether, cationic or amphoteric polymer and/or silicone to the hair dye composition of the present invention is preferred, because the resulting composition can dye the hair uniformly and provides improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, anionic surfactants, protein derivatives, amino acids, antiseptics, chelating agents, stabilizers, antioxidants, plant extracts, crude drug extracts, vitamins, colorants, perfumes and ultraviolet absorbers.

The hair dye composition of the present invention can be prepared in a conventional manner to form a one-part composition or a two-part composition having a first part containing an alkali agent and a second part containing an oxidizing agent. The inventive dyestuff of the general formula (I) may be incorporated in at least one of these parts of the two-part or three-part composition. When the hair dye composition of the present invention is of the one-part type, it is applied to the hair directly, while when it is of the two- or three-part type, these parts are mixed just before hair dyeing and the mixture is applied to the hair.

In the case of preparation of a two-part type hair dye composition, the first part is typically prepared by mixing the Inventive dyestuff of the general formula (I) and optionally an oxidation dye and adjusting the pH of the mixture to 8 to 12 with an alkali agent such as ammonia. The second part is prepared by incorporating about 2 to 6 wt. % of hydrogen peroxide, adjusting the mixture to weakly acidic with phosphoric.

The hair dye composition of the present invention can be provided in the form of powder, transparent liquid, emulsion, cream, gel, paste, aerosol, aerosol foam or the like. It preferably has a viscosity of 2000 to 100000 mPa·s upon its application to the hair (after mixing of all the parts when the composition is a two-part or three-part type). The above-described viscosity is measured at 20° C. by using a Brookfield rotary viscometer (No. 5 spindle, 5 rpm).

The present invention also refers to a process for colouring hair characterized in that a hair dye composition as described above is applied onto hair, left for 1 to 45 minutes and than rinsed off from hair.

In a preferred inventive process the hair dye composition is mixed with a composition comprising at least one oxidizing agent.

In the following, embodiments of the invention are described in detail for the purpose of illustrating only and not for the purpose of limiting the same.

EXAMPLE 1

Preparation of ([3-(4,8-diamino-9,10-dioxo-9,10-dihydro-anthracene-1-ylamino)-propyl]-trimethyl-ammonium methylsulfate)

90 parts of 3-dimethylaminopropylamine, 10.0 parts of 1,5-diamino-4-chloro-anthraquinone and 0.25 parts of Cu(II) acetate were heated together under nitrogen at 110° C. for 7½ hours. After cooling at room temperature, the mixture was poured into 500 parts of cold water. The precipitate was filtered off, washed with water and dried to yield 10.7 parts of a dark blue powder. For quaternisation 9.0 parts of the blue dye thus obtained were dispersed in 100 parts of ethyl alcohol and treated with 3.0 parts of dimethylsulfate. The reaction mixture was stirred for 3½ hours at room temperature. The precipitate was filtered off and washed with acetone. Upon drying 10.7 parts of the dyestuff of the formula Ij were obtained. The blue dye Ij is very good water-soluble. The analytic data are consistent with the assigned structure for dye Ij. $^1$H NMR (500 MHz, DMSO-d6): δ=2.08 (2H), 3.08 (9H), 3.23-3.54 (broad), 7.00 (1H), 7.09 (1H), 7.22 (1H), 7.31-7.53 (broad), 7.75 (2H), 8.19 (2H);

Melting point: >175° C.;

$\lambda_{max}$ (H$_2$O)=584 nm (12500), 626 nm (11600).

EXAMPLE 2

Preparation of ([3-(4-amino-3-methyl-9,10-dioxo-9,10-dihydro-anthracene-1-ylamino)-propyl]-trimethyl-ammonium methylsulfate)

85 parts of 3-dimethylaminopropylamine, 15.8 parts of 1-amino-4-bromo-2-methylanthraquinone and 0.17 parts of Cu(II)acetate were heated together under nitrogen at 94° C. for 2½ hours. After cooling at room temperature, water was added until the product precipitated. The product was filtered off, washed and dried to yield 14.0 parts of a dark violet powder. For quaternisation 10 parts of the violet dye thus obtained were dispersed in 100 parts of chlorobenzene and treated with 2.8 parts of dimethylsulfate. The temperature was increased up to 45° C. and the reaction mixture was kept for 3 hours at this temperature. The precipitate was filtered off at 30° C. and washed with acetone. Upon drying 12 parts of the dye of formula Ia were obtained. The bluish violet dye Ia is very good water-soluble. The analytic data are consistent with the assigned structure for dye Ia.

$^1$H NMR (500 MHz, DMSO-d6): δ=2.10 (2H), 2.33 (3H), 3.09 (9H), 3.39 (3H), 3.42 (2H), 3.50 (2H), 7.32 (1H), 7.78 (2H), 8.23 (2H), 10.83 (1H);

Melting point: >210° C.;

$\lambda_{max}$ (H$_2$O)=564 nm (12600), 605 nm (13300).

EXAMPLE 3

Preparation of ([4-(4-amino-3-methoxy-9,10-dioxo-9,10-dihydro-anthracene-1-ylamino)-phenyl]-trimethyl ammonium methylsulfate)

21.4 parts of 1-amino-4-bromo-9,10-dioxo-9,10-dihydro-anthracene-2-sulfonic acid were dispersed in 100 parts of water at 50° C. Thereafter 9.8 parts of N,N-dimethyl-p-phenylenediamine, 5.0 parts of $NaHCO_3$, 2.7 parts of $Na_2CO_3$ and 0.5 parts of CuCl were added. The reaction mixture was kept at 50-60° C. for 2 hours. After cooling at room temperature, the mixture was poured into 700 parts of 2N HCl. The precipitate was filtered off, washed with water and dried to yield 18.8 parts of a dark blue powder. 9.4 parts of the dyestuff thus obtained were added to a 50° C. warm solution of water-free KOH in methanol. The reaction mixture was kept at 50° C. for 6 hours. After cooling off, the mixture was poured into 200 parts of water and treated with conc. HCl to a pH value of 6.5-7.0. The precipitate was filtered off, washed with water and dried to yield 7.5 parts of a blue powder. To quaternisation 7.0 parts of this dye dispersed in 95 parts of chlorobenzene were treated with 8.1 parts of dimethylsulfate and stirred at 80° C. for 7 hours. The reaction mixture was filtered off at room temperature, washed with chloroform and dried to obtain 9.05 parts of the dye of formula Ib, which dissolves in water with blue color. The analytic data are consistent with the assigned structure for dye Ib.

$^1$H NMR (500 MHz, DMSO-d6): δ=3.25 (3H), 3.63 (9H), 3.88 (3H), 7.51 (1H), 7.62 (2H), 7.83 (2H), 7.96 (2H), 8.23 (2H), 12.68 (1H);

Melting point: >166° C.;

$\lambda_{max}$ ($H_2O$)=574 nm (9000), 605 nm (8000).

EXAMPLE 4

Preparation of ([3-(4-amino-3-ethyl-9,10-dioxo-9,10-dihydro-anthracene-1-ylamino)-propyl]-trimethyl-ammonium methylsulfate)

10.5 parts of 3-dimethylaminopropylamine, 15.0 parts of 1-amino-4-bromo-2-ethyl-anthraquinone, 6.2 parts of water free $K_2CO_3$ and 0.20 parts of Cu(II)acetate in 55 parts of dimethylformamide were heated under nitrogen at 80° C. for 3½ hours. After cooling at room temperature, the mixture was poured into 350 parts of cold water as the product precipitated. The product was filtered off, washed and dried to yield 14.10 parts of a dark violet powder. For quaternisation 13.0 parts of the violet dye thus obtained were dispersed in 160 parts of chlorobenzene and treated with 2.3 parts of dimethylsulfate during 30 min. The temperature was increased up to 40-45° C. and the reaction mixture was kept for 3 hours at this temperature. The precipitate was filtered off at 30° C. and washed with warm chlorobenzene. Upon drying 11.9 parts of the dye of formula Is were obtained. The bluish violet dye Is is very good water-soluble. The analytic data are consistent with the assigned structure for dye Is.

$^1$H NMR (500 MHz, DMSO-d6): δ=1.25 (3H), 2.12 (2H), 2.72 (2H), 3.10 (9H), 3.38 (3H), 3.44 (2H), 3.53 (2H), 7.24 (1H), 7.79 (2H), 8.24 (2H), 10.87 (1H);

Melting point: >117° C.;

$\lambda_{max}$ ($H_2O$)=565 nm (10200), 605 nm (10600).

EXAMPLE 5

Preparation of ([2-(4-amino-3-methyl-9,10-dioxo-9,10-dihydro-anthracene-1-yloxy)-ethyl]-trimethyl-ammonium methylsulfate)

3.1 parts of 1-amino-4-(2-dimethylamino-ethoxy)-2-methylanthraquinone prepared from 1-amino-4-chloro-2-methylanthraquinone, N N-dimethylaminoethanolamine and metallic sodium at 95° C. were dispersed in 40 parts of chlorobenzene and treated with 1.0 part of dimethylsulfate. The reaction mixture was kept for 1 hour at room temperature. The precipitate was filtered off and washed with acetone. Upon drying 3.3 parts of the dye of formula If were obtained. The red dye If is very good water-soluble. The analytic data are consistent with the assigned structure for dye If.

$^1$H NMR (500 MHz, DMSO-d6): δ=2.30 (3H), 3.33 (9H), 3.38 (3H), 3.84 (2H), 4.50 (2H), 7.50 (1H), 8.07 (2H), 8.17 (2H);

Melting point: >224° C.;

$\lambda_{max}$ ($H_2O$)=501 nm (5600).

EXAMPLE 6

Preparation of ([2-(4,8-diamino-9,10-dioxo-9,10-dihydro-anthracene-1-yloxy)-ethyl]-trimethyl-ammonium methylsulfate)

6.6 parts of 1,5-diamino-4-(2-dimethylamino-ethoxy)-anthraquinone prepared from 1,5-diamino-4-chloro-anthraquinone, N,N-dimethylaminoethanolamine and metallic sodium at 95-120° C. were dispersed in 75 parts of chlorobenzene and treated with 1.4 parts of dimethylsulfate. The reaction mixture was kept for 1½ hours at room temperature. The precipitate was filtered off and stirred with 150 parts of water followed by filtration. The filtrate was evaporated in vacuo yielding 2.5 parts of the dye of formula Ik. The red dye Ik is very good water-soluble. The analytic data are consistent with the assigned structure for dye Ik.

$^1$H NMR (500 MHz, DMSO-d6): δ=3.29 (9H), 3.38 (3H), 3.83 (2H), 4.42 (2H), 7.08 (1H), 7.18 (1H), 7.33 (1H), 7.43-7.48 (2H), 7.73 (2H), 7.92 (2H);

Melting point: >114° C.;

$\lambda_{max}$ ($H_2O$)=508 nm (10000).

EXAMPLE 7

Preparation of ([3-(4-amino-3-carbamoyl-9,10-dioxo-9,10-dihydro-anthracene-1-ylamino)-propyl]-trimethyl-ammonium methylsulfate)

8.9 parts of 1-amino-4-(3-dimethylamino-propylamino)-9,10-dioxo-9,10-dihydro-anthracene-2-carboxylic acid amide were dispersed in 85 parts of o-dichlorobenzene and treated with 2.1 parts of dimethylsulfate at 50° C. The reaction mixture was kept at this temperature for 2 hours. The precipitate was filtered off and washed with warm o-dichlorobenzene and afterwards with ethyl acetate. Upon drying 10.8 parts of the dye of formula Ig were obtained. The blue dye Ig very good water-soluble. The analytic data are consistent with the assigned structure for dye Ig.

$^1$H NMR (500 MHz, DMSO-d6): δ=2.13 (2H), 2.33 (3H), 3.10 (9H), 3.38 (3H), 3.42 (2H), 3.58 (2H), 7.63 (1H), 7.83 (2H), 8.23 (2H), 10.53 (1H);

Melting point: >93° C.;

$\lambda_{max}$ ($H_2O$)=597 nm (11200), 621 nm (11300).

EXAMPLE 8

Preparation of ([3-(4,8-diamino-3-methoxy-9,10-dioxo-9,10-dihydro-anthracene-1-ylamino)-propyl]-trimethyl-ammonium methylsulfate)

2.44 parts of 1,5-diamino-4-(3-dimethylamino-propylamino)-2-methoxy-anthraquinone prepared from 1,5-diamino-4-(3-dimethylamino-propylamino)-9,10-dioxo-9,10-dihydro-anthracene-2-sulfonic acid and methanolic potassium hydroxide at 95° C. were dispersed in 50 parts of diglyme and treated with 0.75 part of dimethylsulfate. The reaction mixture was kept for 3 hours at room temperature. The precipitate was filtered off and washed with acetone. Upon drying 2.8 parts of the dye of formula Iz were obtained. The blue dye Iz is very good water-soluble. The analytic data are consistent with the assigned structure for dye Iz.

$^1$H NMR (500 MHz, DMSO-d6): δ=2.12 (2H), 2.33 (3H), 3.10 (9H), 3.39 (3H), 3.43 (2H), 3.50 (2H), 4.02 (3H), 6.65 (1H), 6.99 (1H), 7.39 (2H), 10.75 (1H);

Melting point: >120° C.;

$\lambda_{max}$ (H$_2$O)=569 nm (13300), 606 nm (11500).

The inventive dyestuffs listed in Table 1 below were synthesized in analogy to the procedures described in examples 1 to 8. Q always denotes —N$^+$(CH3)3. The dyestuffs were isolated in form of their methylsulfate salts.

TABLE 1

| Example | R | X | Y | Z | Colour (aqeous solution) |
|---|---|---|---|---|---|
| 9 | —CH$_2$CH$_2$OH | —CH$_3$ | —NH(CH$_2$)$_3$-Q | H | bright blue |
| 10 | —C$_6$H$_5$ | " | " | " | " |
| 11 | —C$_6$H$_{11}$ | " | " | " | " |
| 12 | —CH(CH$_3$)$_2$ | " | " | " | " |
| 13 | —CH$_2$CH$_2$OH | —CH$_2$CH$_3$ | " | " | " |
| 14 | —C$_6$H$_5$ | " | " | " | " |
| 15 | —C$_6$H$_{11}$ | " | " | " | " |
| 16 | —CH(CH$_3$)$_2$ | " | " | " | " |
| 17 | H | —COCH$_3$ | " | " | " |
| 18 | H | —CH$_3$ | —NH—C$_6$H$_4$—CH$_2$-Q | " | reddish blue |
| 19 | —CH(CH$_3$)$_2$ | H | —NH(CH$_2$)$_3$-Q | 5-OH | blue |
| 20 | —CH$_2$CH$_2$OH | —CONH$_2$ | " | H | greenish blue |
| 21 | —(CH2)$_3$-Q | —CH$_3$ | —NH—C$_6$H$_5$ | H | blue |
| 22 | —(CH$_2$)$_3$-Q | —CH$_3$ | —NH—C$_6$H$_4$—CH$_3$ | H | greenish blue |
| 23 | H | H | —NH—C$_6$H$_4$—CH$_2$-Q | 5-NH$_2$ | greenish blue |
| 24 | —CH$_2$CH$_2$OH | —COOEt | —NH(CH$_2$)$_3$-Q | H | greenish blue |
| 25 | H | —CONH$_2$ | —NH—C$_6$H$_4$—CH$_2$-Q | H | greenish blue |
| 26 | H | —COOEt | " | H | greenish blue |
| 27 | H | —CONH$_2$ | —O(CH$_2$)$_2$-Q | H | bluish red |
| 28 | H | —COOEt | —O(CH$_2$)$_2$-Q | H | bluish red |
| 27 | —CH(CH$_3$)$_2$ | H | " | -5-OH | red |
| 28 | H | —SO$_2$NHCH3 | —NH(CH$_2$)$_3$-Q | H | greenish blue |
| 29 | H | —SO$_2$NH$_2$ | —O(CH$_2$)$_2$-Q | H | bluish red |
| 30 | H | —OMe | —NH(CH$_2$)$_3$-Q | 7-OMe | reddish blue |
| 31 | H | —OMe | —NH—C$_6$H$_4$—CH$_2$-Q | H | reddish blue |
| 32 | H | —O(CH$_2$)$_2$OH | " | H | reddish blue |
| 33 | H | —CH$_3$ | —N(CH$_3$)(CH$_2$)$_3$-Q | H | blue |
| 34 | H | H | —O(CH$_2$)$_2$-Q | 5-NHAc | red |
| 35 | H | H | " | 5-NH2 | bluish red |
| 36 | —CH$_3$ | H | —NH(CH$_2$)$_3$-Q | 5-NHCH$_3$ | dark blue |
| 37 | —(CH$_2$)$_3$-Q | —CH$_3$ | —OH | H | bluish red |
| 38 | H | —CN | —NH(CH$_2$)$_3$-Q | H | blue |
| 39 | H | —CH=N—C$_6$H$_5$ | " | H | blue |
| 40 | H | —CH=N—C$_6$H$_5$ | —O(CH$_2$)$_2$-Q | H | red |
| 41 | —CH$_2$CH$_2$OH | H | —NH(CH$_2$)$_3$-Q | 5-NHC$_2$H$_4$OH | blue |

Examples of Dyeing Performance of Dyestuffs

Example A

The dyes listed in Table 2 were dissolved into the following Base Formulation 1:

| Dyestuff of general formula (I) | 0.5 g |
|---|---|
| iso-Propanol | 5.0 g |

-continued

| | |
|---|---|
| Ammonium Hydroxide (25%) | 5.0 g |
| Water | up to 100 g |
| pH | 10.2 |

Approximately 1.5 g of the Base Formulation I was applied to 1 g of undamaged white goat hair at 30° C. for 30 mins. At the end of the processing time the tresses were rinsed with water, shampooed and then dried.

The colour of the tresses was recorded by measuring L, a and b values of the tresses before and after the colouring using a hand held Datacolor Mercury colour-measuring instrument and the value of delta E, which is a known measure for the chroma, was calculated according to the well-known equation: $\Delta E = (\Delta L^2 + \Delta a^2 + \Delta b^2)^{1/2}$ for each example (this will apply equally to every example hereinafter).

The results are shown in Table 2: Dyeing effect of Examples (Ia), (Ib), (Id), (ID, (Ij), (Ik and (Im) on undamaged goat hair:

TABLE 2

| Dyestuff | Color of Dyed Hair | L | a | b | Delta E |
|---|---|---|---|---|---|
| Formula Ij | Vivid Cyan Blue | 40.4 | −3.0 | −20.3 | 53.7 |
| Formula Ia | Intense Pure Blue | 48.8 | 5.2 | −24.6 | 50.4 |
| Formula Id | Violet Blue | 40.4 | 5.5 | −16.6 | 51.6 |
| Formula Ib | Intense Ash Blue | 47.4 | −1.3 | −14.7 | 44.7 |
| Formula If | Red Brown | 46.4 | 21.9 | 7.7 | 42.9 |
| Formula Ik | Pure Red | 44.0 | 39.5 | 8.1 | 54.9 |
| Formula Im | Dark Violet | 43.5 | 10.7 | −15.0 | 49.5 |

Example B

The dyes listed in Table 3 were dissolved into the following Base Formulation 2, containing alkaline hydrogen peroxide:

| | |
|---|---|
| Dyestuff of general formula (I) | 0.5 g |
| iso-Propanol | 5.0 g |
| Ammonium Hydroxide (25%) | 5.0 g |
| Hydrogen Peroxide (50%) | 6.0 g |
| Water | up to 100 g |
| pH | 10.2 |

Approximately 1.5 g of the Base Formulation 2 was applied to 1 g of undamaged white goat hair at 30° C. for 30 mins. At the end of the processing time the tresses were rinsed with water, shampooed and then dried. The color of the tresses was recorded as given in Example A above.

The results are shown in Table 3: Dyeing effect of Examples (Ia), (Ib), (Id), (If), (Ij), (Ik) and (Im) on undamaged goat hair in combination with alkaline peroxide:

TABLE 3

| Dyestuff | Color of Dyed Hair | L | a | b | Delta E |
|---|---|---|---|---|---|
| Formula Ij | Vivid Cyan Blue | 40.4 | −3.0 | −20.3 | 53.7 |
| Formula Ia | Intense Pure Blue | 48.8 | 5.2 | −24.6 | 50.4 |
| Formula Id | Violet Blue | 40.4 | 5.5 | −16.6 | 51.6 |
| Formula Ib | Intense Ash Blue | 47.4 | −1.3 | −14.7 | 44.7 |
| Formula If | Red Brown | 46.4 | 21.9 | 7.7 | 42.9 |
| Formula Ik | Pure Red | 44.0 | 39.5 | 8.1 | 54.9 |
| Formula Im | Dark Violet | 43.5 | 10.7 | −15.0 | 49.5 |

The invention claimed is:

1. A mixture comprising one or more dyestuffs of of formula (I)

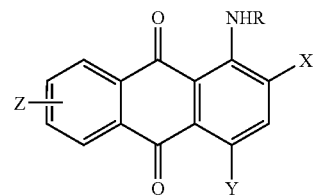

(I)

wherein

R is hydrogen, alkyl, alkyl substituted by Q, aryl, Q-aryl, —$OR^2$, —$SR^3$ or —$NR^5R^4$, hydroxyalkyl, hydroxyalkyl substituted in the alkyl group by Q, polyhydroxyalkyl, polyhydroxyalkyl substituted in the alkyl group by Q, cycloalkyl, cycloalkyl substituted by Q, aryl substituted by $R^{10}$, Q, $R^{11}$O-alkyl, —$OR^{12}$, —$SR^{13}$, —$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$, —$C(O)R^6$, —$SO_2NR^7R^8$ or —$SO_2R^9$;

X is hydrogen, —$OR^{23}$, —$SR^{24}$, —$NR^{25}R^{26}$, —$SO_2NR^{27}R^{28}$, —$CONR^{29}R^{30}$, —$SO_2R^{31}$, —$C(O)OR^{32}$, —$C(O)R^{33}$, —$SO_2R^{34}$, alkyl, alkyl substituted by —$OR^{200}$, —$SR^{300}$ or —$NR^{500}R^{400}$, aryl substituted by $R^{100}$, $R^{110}$O-alkyl, —$OR^{120}$, —$SR^{130}$, —$NR^{140}R^{150}$, —$CONR^{150}R^{160}$, —$C(O)OR^{170}$, —$SO_2$—$NR^{180}R^{190}$, —$SO_2OR^{201}$, —$C(O)R_{210}$ or —$SO_2R^{220}$, —$NHSO_2R^{37}$, —CHO, —CH=$NR^{35}$ or $NO_2$;

Y is hydrogen, —$NR^{51}R^{52}$, —$OR^{53}$, —$SR^{54}$, —$SO_2NHR^{55}$, —$NHC(O)R^{56}$, —$SO_2OR^{57}$, —$NHSO_2R^{58}$, —$SO_2R^{59}$, —$NHSO_2NR^{60}R^{61}$, halogen or $NO_2$;

Z is hydrogen, —$NR^{51}R^{52}$, —$OR^{53}$, —$SR^{54}$, —$SO_2NHR^{55}$, —$NHC(O)R^{56}$, —$SO_2OR^{57}$, —$NHSO_2R^{58}$, —$SO_2R^{59}$, —$NHSO_2NR^{60}R^{61}$, halogen or $NO_2$;

each of $R^2$ to $R^8$ $R^{60}$ and $R^{61}$, independently, is hydrogen, alkyl, alkyl substituted by Q, aryl, aryl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

$R^9$ is alkyl, alkyl substituted by Q, aryl, aryl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{10}$ to $R^{16}$, $R^{18}$, $R^{19}$ and $R^{21}$, independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{17}$, $R^{20}$ and $R^{22}$, independently, is alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q;

each of $R^{23}$ to $R^{30}$ and $R^{35}$, independently, is hydrogen, alkyl, hydroxyalkyl, polyhydroxyalkyl, cycloalkyl or cycloalkyl substituted by —$C(O)R^6$, —$SO_2R^9$, or aryl substituted by $R^{10'}$, $R^{11'}$ O-alkyl, —$OR^{12'}$, —$SR^{13'}$ —$NR^{14'}R^{15'}$, —$CONR^{15'}R^{16'}$, —$C(O)OR^{17'}$, $SO_2$—$NR^{18'}R^{19'}$, —$SO_2OR^{20'}$, —$C(O)R^{21'}$ or —$SO_2R^{22'}$;

$R^6$ is hydrogen, alkyl, aryl, hydroxyalkyl, polyhydroxyalkyl or cycloalkyl;

$R^9$ is alkyl, aryl, hydroxyalkyl, polyhydroxyalkyl or cycloalkyl;

each of $R^{10'}$ to $R^{16'}$, $R^{18'}$, $R^{19'}$ and $R^{21'}$, independently, is hydrogen, alkyl, hydroxyalkyl, polyhydroxyalkyl or cycloalkyl;

each of $R^{17'}$, $R^{20'}$ and $R^{22'}$, independently, is alkyl, hydroxyalkyl, polyhydroxyalkyl or cycloalkyl;

each of $R^{36}$ and $R^{37}$, independently, is alkyl, aryl, hydroxyalkyl, polyhydroxyalkyl or cycloalkyl and one of $R^{36}$ and $R^{37}$ can additionally be hydrogen; each of $R^{51}$ to $R^{54}$, independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q, —$C(O)R^6$, —$SO_2R^9$ or aryl substituted by $R^{10}$, $R^{11}O$-alkyl, —$OR^{12}$, $SR^{13}$, —$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$;

each of $R^{31}$ to $R^{33}$, independently, is alkyl, hydroxyalkyl, polyhydroxyalkyl, cycloalkyl or aryl substituted by $R^{10'}$, $R^{11'}$O-alkyl, —$OR^{12'}$, —$SR^{13'}$, —$NR^{14'}R^{15'}$, —$CONR^{15'}R^{16'}$, —$C(O)OR^{17'}$, —$SO_2$—$NR^{18'}R^{19'}$, —$SO_2R^{20'}$, —$C(O)R^{21'}$ or —$SO_2R^{22'}$, and $R^{33}$ can additionally be hydrogen;

$R^{34}$ is alkyl, hydroxyalkyl, polyhydroxyalkyl, cycloalkyl or aryl substituted by $R^{10'}$, $R^{11'}$O-alkyl, —$OR^{12'}$, —$SR^{13'}$, —$NR^{14'}R^{15'}$, —$CONR^{15'}R^{16'}$, —$C(O)OR^{17'}$, $SO_2$—$NR^{18'}R^{19'}$, —$SO_2OR^{20'}$, —$C(O)R^{21'}$ or —$SO_2R^{22'}$;

each of $R^{55}$ to $R^{57}$, independently, is hydrogen, alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q or aryl substituted by $R^{10}$, $R^{11}O$-alkyl, —$OR^{12}$, —$SR^{13}$, —$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$, and $R^{55}$ and $R^{56}$ can additionally be hydrogen;

each of $R^{58}$ and $R^{59}$, independently, is alkyl, alkyl substituted by Q, hydroxyalkyl, hydroxyalkyl substituted in the alkyl group by Q, polyhydroxyalkyl, polyhydroxyalkyl substituted in the alkyl group by Q, cycloalkyl or cycloalkyl substituted by Q or aryl substituted by $R^{10}$, $R^{11}O$-alkyl, —$OR^{12}$, —$SR^{13}$, —$NR^{14}R^{15}$, —$CONR^{15}R^{16}$, —$C(O)OR^{17}$, —$SO_2$—$NR^{18}R^{19}$, —$SO_2OR^{20}$, —$C(O)R^{21}$ or —$SO_2R^{22}$;

each of $R^{200}$, $R^{300}$, $R^{400}$ and $R^{500}$, independently, is hydrogen, alkyl, aryl, hydroxyalkyl, polyhydroxyalkyl or cycloalkyl; each of $R^{100}$, $R^{110}$, $R^{120}$, $R^{130}$, $R^{140}$, $R^{150}$, $R^{150}$, $R^{180}$, $R^{190}$ and $R^{210}$ independently, is hydrogen, alkyl, hydroxyalkyl, polyhydroxyalkyl, or cycloalkyl;

each of $R^{170}$, $R^{201}$, and $R^{220}$, independently, is alkyl, hydroxyalkyl, polyhydroxyalkyl, or cycloalkyl; and Q is a group of formula (II)

wherein each of R', R'' and R''', independently, is ($C_1$-$C_6$)-alkyl, aryl, arylalkyl, cycloalkyl, cycloalkylalkyl, heteroaryl, heteroarylalkyl, heterocycloalkyl, heterocycloalkyl-alkyl, either of which can be substituted by a heteroatom comprising groups or R' and R'' form together with the nitrogen to which they are bonded a 5- or 6- membered satureated heterocyclic ring; and $A^-$ is a cosmetically acceptable, water solubilizing anion, and does not comprise arylsulfonate, phosponate and alkylphosphonate;

whereby the dyestuff of the formula (I) comprises exactly one group Q;

whereby at least two of the groups X, Y and Z are groups other than hydrogen; and whereby in case R and X are both hydrogen and Y is —$NR^{51}R^{52}$ or —$OR^{23}$, wherein $R^{51}$, $R^{52}$ and $R^{23}$ are hydrogen, Z is not —$NR^{25}R^{26}$, wherein one of $R^{25}$ and $R^{26}$ is hydrogen and the other is alkyl substituted by Q.

2. A hair dye composition comprising one or more dyestuffs of formulae (I) according to claim 1 or a mixture comprising one or more dyestuffs of formula (I) and one or more direct or oxidation dyestuff.

3. The hair dye composition according to claim 2 which further comprises at least one oxidative dye precursor, at least one coupling compound, or a combination thereof.

4. The hair dye composition according to claim 2 which comprises an oxidizing agent.

5. The hair dye composition according to claim 2 which has a pH value in the range of 2 to 11.

6. A process for colouring hair comprising: (1) applying the hair dye composition according to claim 2 onto hair for 1 to 45 minutes, and (2) rinsing off said hair dye composition from said hair.

\* \* \* \* \*

UNITED STATES PATENT AND TRADEMARK OFFICE
CERTIFICATE OF CORRECTION

PATENT NO. : 7,776,106 B2
APPLICATION NO. : 12/279003
DATED : August 17, 2010
INVENTOR(S) : Roxana Barbieru et al.

Page 1 of 1

It is certified that error appears in the above-identified patent and that said Letters Patent is hereby corrected as shown below:

Column 22, lines 34 (Claim 1) "alkyl substituted by Q." should read

-- alkyl substituted by Q and one or more direct or oxidation dyestuff. --

Signed and Sealed this

Twenty-third Day of November, 2010

David J. Kappos
*Director of the United States Patent and Trademark Office*